United States Patent [19]

Karr, Jr.

[11] Patent Number: 4,814,170

[45] Date of Patent: Mar. 21, 1989

[54] METHOD FOR IMMUNIZATION AGAINST AND TREATMENT OF INFECTION BY ECTOPARASITES AND ENDOPARASITES

[75] Inventor: Stephen L. Karr, Jr., Davis, Calif.

[73] Assignee: Aphton Corporation, Woodland, Calif.

[21] Appl. No.: 839,892

[22] Filed: Mar. 14, 1986

[51] Int. Cl.$^4$ ............................................. A61K 37/24
[52] U.S. Cl. .................................... 424/88; 424/85; 424/95; 514/2; 514/12; 514/21
[58] Field of Search ................. 424/85, 88, 95; 514/2, 514/12, 21

[56] References Cited

U.S. PATENT DOCUMENTS

| | | | |
|---|---|---|---|
| 3,395,218 | 7/1968 | Silverman | 424/88 |
| 3,746,490 | 7/1973 | Marsland et al. | 514/146 |
| 3,874,533 | 4/1975 | Carr et al. | 414/3 |
| 4,036,987 | 7/1977 | Thompson et al. | 514/671 |
| 4,374,853 | 2/1983 | Workman | 514/506 |

OTHER PUBLICATIONS

Khalil et al. C.A., vol. 101, 1984, #224759w.
Khalil et al., C.A., vol. 100, 1984, #204949j.
Connat et al., C.A., vol. 100, 1984, #189112r.
Campbell et al., C.A., vol. 101, 1984, #148457d.
Lee et al., C.A., vol. 103, 1985, #212924z.
Heinz et al., C.A., vol. 102, 1985, #4251e.
Palmer et al., C.A., vol. 104, 1986, #32786e.
Abdelmanem et al., C.A., vol. 105, 1986, #2194b.
Galum, 1975, Proceeding Workshop on Ecology . . . Latin America.
Koolman et al., 1984, Metabolism and Mode of Action . . . Hormones, pp. 323-330.
Hirn et al., Progress in Ecdysone Research (1980).
Reum et al., Insect Biochem., vol. 9, pp. 135-142 (1979).
Maroy, FEBS Letters, vol. 81, No. 2, pp. 319-322 (1977).
Horn et al., Insect. Physiol., vol. 22, pp. 901-905.
Strambi et al., Eur. J. Biochem., 118, pp. 401-406 (1981).
Baehr et al., FEBS Letters, vol. 69, No. 1, pp. 123-128 (1976).
Dennis, International Journal for Parasitology, vol. 7, pp. 171-179 (1977).
Boisvenue et al., Experimental Parasitology, 42, 67-72 (1977).
Hitcho et al., The J. of Parasitology, vol. 57, No. 4, pp. 787-793 (1971).
Dennis, Comp. Biochem. Physiol., vol. 53A, pp. 53-56 (1976).
Davey, Biochemistry of Parasites and Host-Parasite Relationships, pp. 359-375 Van den Boshe, Ed. Elsevier.
Mango, Tick Borne Diseases and Their Vectors, pp. 35-37.
Davey, International Journal for Parasitology, vol. 1, pp. 61-66 (1971).
Hansen et al., Experientia 27, 7 859-860 (1971).
Bottjer et al., Comp. Biochem. Physiol., vol. 82B, No. 1, pp. 99-106 (1985).
Feldmesser et al., Experientia 32/4, pp. 466-467 (1976).
Goodman & Gilman's, the Pharmacological Basis of Therapeutics, 6th Ed., pp. 1013-1079 (1980).
Van Nostrand's Scientific Encyclopedia, 6th Ed., pp. 1620-1625 (1983).
F. W. Douvres et al., Veterinary Parasitology, I, pp. 195-205 (1980).
G. H. Glassburg et al., Proc. Helm. Soc. Wash., 50, pp. 62-68 (1983).
Khalil et al., J. Med. Entomol, vol. 21, Nos. 5:561-566 and 2:188-193, (1984).
Campbell et al., Acarology VI, vol. 1, pp. 393—399 (1984).

*Primary Examiner*—Johnnie R. Brown
*Assistant Examiner*—Garnette D. Draper
*Attorney, Agent, or Firm*—Dimitrios T. Drivas; Irene J. Frangos

[57] ABSTRACT

This invention relates to a method for the active or passive immunization of a vertebrate against ectoparasites and endoparasites, and a method of treating a vertebrate host infected by ectoparasites or endoparasites, comprising administering to the vertebrate an immunogen comprising one or more endocrine products of ectoparasites and endoparasites, coupled with an immunogenic carrier, or administering to the vertebrate, monoclonal antibodies formed to said immunogen.

1 Claim, No Drawings

METHOD FOR IMMUNIZATION AGAINST AND TREATMENT OF INFECTION BY ECTOPARASITES AND ENDOPARASITES

TECHNICAL FIELD OF THE INVENTION

This invention relates to an immunotherapeutic treatment against infection by ectoparasites and endoparasites. Additionally, this invention relates to a method for active or passive immunization against ectoparasites and endoparasites comprising treating a vertebrate with the endocrine products of ectoparasites and endoparasites coupled with an immunogenic carrier. According to this invention, anti-parasitic growth regulator antibodies are used to actively or passively immunize a vertebrate against and to eliminate infection by ectoparasites and endoparasites.

BACKGROUND OF THE INVENTION

This invention relates to the use of invertebrate growth regulators, neurohormones, and other invertebrate endocrine products as vaccine components to actively immunize a vertebrate against ectoparasites and endoparasites, and as medicaments to treat a vertebrate infected by said parasites.

Conventional attempts to prevent, or rid a host of, infection by ectoparasites and endoparasites (hereinafter also referred to as target parasites) have involved treatment of a susceptible or infected host (e.g., mammal) with anthelmintic chemicals [see generally, Goodman and Gilman's, The Pharmacologicol Basis of Therapeutics, 6th Ed., pp. 1013–79 (1980)]. For example, U.S. Pat. No. 3,746,490 refers to a method for controlling instar bot larvae and endoparasites in horses comprising applying a paste containing dimethyl-1-dichlorovinyl phosphate into the mouth of a horse; U.S. Pat. No. 3,879,533 refers to the control of endoparasitic nematodes by 3-phenyl-5-(halo-, alkylthio- or alkoxy)-isoxazoles; U.S. Pat. No. 4,036,987 refers to the control of nematodes and other helminths using secondary and tertiary straight end branched chain amides and amines; and U.S. Pat. No. 4,374,853 refers to a method for controlling mammalian ectoparasites, such as fleas and ticks, using an aqueous antiseptic liquid. Typically these treatments are characterized by various undesirable side effects, such as short periods of sensitivity, toxic build-up of chemicals, a need to re-treat animals and the development of resistance to chemicals by the targetted parasites.

In view of the disadvantages of such therapies, various other methods of protecting mammals from ectoparasitic and endoparasitic infection have been attempted. For example, U.S. Pat. No. 3,395,218 refers to a method of immunization using nematode surface antigens formed from the ex-sheathment of larvae. More recently, attempts have been made to use ecdysone or juvenile hormones and their analogues to disrupt directly the development of helminth endoparasites. For example, when juvenile hormones are administered to the infected host during metamorphosis (larvae into adult) the adult endoparasites produced are deformed and lack the capacity for further development and soon die [see generally, Van Nostrand's *Scientific Encyclopedia*, 6th Ed. pp. 1620–25 (1983); F. W. Douvres et al., "In Vitro Cultivation Of Ostertagia ostertagi, The Medium Stomach Worms Of Cattle. II. Effect of Insect-Growth-Disrupting Amines And Amides On Development," *Veterinary Parasitology*, 1, pp. 195–205 (1980); G. H. Glassburg et al., "Juvenoid effects on *Nippostrongylus brasiliensis* and *Heterodera glycines* (Nematoda)," *Proc. Helm. Soc. Wash.*, 50, pp. 62–68 (1983)]. However, such treatment is not very reliable because effectiveness is limited to the relatively short period of metamorphosis; if the juvenile hormones are applied before or after this period, they are ineffective. Furthermore, such treatment would have to be repeated frequently and, because of inefficient tissue distribution in the infected host, may not even reach and be absorbed by the infected tissue.

SUMMARY OF THE INVENTION

The present invention relates to a method of actively or passively immunizing a vertebrate against infection by ectoparasites or endoparasites and a method of treating a vertebrate infected by ectoparasites or endoparasites, comprising administering to said vertebrate an effective amount of an immunogen comprising an endocrine product of said ectoparasite or endoparasite coupled with an immunogenic carrier. According to the present invention, a susceptible or compromised vertebrate is immunized, or treated, using a vaccine or medicament, respectively, formed from a preparation of parasite hormones. The vaccines or medicaments of the present invention may be used to induce an active immune response in a potential vertebrate target or host so that specific antibodies are raised against the targetted parasitic hormone that will bind to and block the activity of that hormone so that the parasites fail to develop, and then die. Alternatively, monoclonal antibodies, prepared in vitro, which are specific for the targetted parasitic hormone may be administered directly to passively immunize the vertebrate.

The present invention also comprises a vaccine or medicament comprising the aforementioned immunogen and a pharmaceutically acceptable carrier (e.g., sterile saline) and optionally also comprising a suitable adjuvant (e.g., alum).

DETAILED DESCRIPTION OF THE INVENTION

In order that the invention herein described may be more fully understood, the following detailed description is set forth. In the description, the following terms are set forth:

ECTOPARASITE—An ectoparasite is a parasite which lives on the outside of the body of the host. Examples of ectoparasites are insects of the order Siphonaptera, commonly known as fleas, and the blood-sucking acarid parasites of the suborder Ixodides, superfamily Ixodoidea, commonly known as ticks.

ENDOPARASITE—An endoparasite is a parasite that lives within the body of its host. Examples of endoparasites are any of the families of parasitic flatworms (Phyla Platyhelminthes, e.g., Trematoda and Cestoda), roundworms (Aschelminthes, e.g., Nematoda), and the larval forms of certain flies that cause myiasis.

ENDOCRINE PRODUCT—As used in this description, an endocrine product includes natural hormones, hormone-like polypeptides or fragments thereof possessing the antigenic characteristics of the targetted hormone.

JUVENILE HORMONES—Juvenile Hormones (JH) are organic compounds involved in the growth, development and reproduction of insects, which are present in insects during the greater part of their development. As used in this description, "JH" refers to acyclic sesquiterpenes, which are secreted by the "corpus allatum" gland located behind the brain [see J. C. Baehr et al., "A Simple And Sensitive Insect Juvenile Hormone Using An Iodinated Tracer," *FEBS Letters*, 69, pp. 123-28 (1976)]. JH are known to control development in insects from larvae to adult stages and development of eggs into adult insects [see W. W. Doane, *Developmental Systems*, 2, pp. 291-497 (173)]. In the adult insect, JH are secreted again and act as gonadotropic hormones by stimulating vitellogenesis and activities of the accessory glands [see F. Engelmann, *The Physiology of Insect Reproduction* (1970)]. A similar control of development and reproduction has been indicated for nematodes [W. P. Rogers, "Juvenile and Moulting Hormones From Nematodes, *Parasitology*, 67, pp. 105-13 (1973)].

ECDYSONE—Ecdysone is a molting hormone, which initiates the moulting process and induces a larval molt with a high JH titer [see Peter Maroy et al., "Rapid Heterologous Haptene Radioimmunoassay For Insect Moulting Hormone," *FEBS*, 81, pp. 319-22 (1977)]. As used in this application, the term ecdysone includes both alpha-ecdysone and beta-ecdysone, which is commonly known as either ecdysterone or 20-hydroxy ecdysone.

PEPTIDE HORMONES—Peptide hormones are a diverse group of hormones, made up of covalently linked amino acids. As used in this application, the term peptide hormones includes, but is not limited to, proctolin, an insect neurotransmitter, and adipokinetic hormone, a hormone which controls fat metabolism in insects.

IMMUNIZATION—The process of eliciting a humoral immune response by an antigen or hapten, i.e., active immunization; or supplementing the body's immune system by administering antibodies formed to that antigen or hapten (i.e., passive immunization).

The present invention relates to a process for active or passive immunization against parasites and treatment of a vertebrate compromised by parasitic infection. The process comprises administering to a potential target or compromised vertebrate host, an endocrine product of ectoparasites or endoparasites which has been conjugated to an immunogenic carrier. Alternatively, the process comprises the step of administering preformed antibodies to a target or compromised host by oral or parenteral route. The resultant vaccine or medicament can then be used to elicit an active or passive immune response against the target parasite.

This invention takes advantage of the need of the target parasites to pass through developmental stages (molts) in the host. These molts are controlled, in part, by hormones. Vaccination of the host with these hormones results in the production of a host immune response that blocks the activity of these parasitic hormones and causes a failure of the parasite to develop and its subsequent death.

Metazoan parasites which contain target hormones potentially useful in the practice of the present invention include representatives of the Phyla Platyhelminthes (e.g., Trematoda and Cestoda), Aschelminthes (e.g., Nematoda), and Arthropoda (e.g., Insecta).

Parasitic hormones demonstrated to be present in the aforementioned metazoan parasites and potentially useful as immunogens in the vaccines of the present invention include the steroids alpha-ecdysone and beta-ecdysone; the terpenoid juvenile hormones (JH), e.g., $JH_{1-3}$, and their structural analogues; and several peptide hormones of varying structure, including shrimp red pigment concentrating hormone, proctolin, adipokinetic hormone, *Drosophila* paragonial peptide, and their structural analogues.

Several linking (conjugation) methods for linking the hormone to an immunogenic carrier are known to those skilled in the art of preparing conjugates for immunoassays, for example. They include, for example, the known carbodiimide method (see below, Examples 1, 2 and 4) for coupling alpha-ecdysone or beta-ecdysone and the juvenile and peptide hormones to a carrier and the known carboxymethoxylamine method (see below, Example 3) for coupling beta-ecdysone to a carrier. The appropriate linking method may be used to prepare an activated hormone intermediate. The intermediate is then linked with a suitable protein carrier, such as, but not limited to, Keyhole Limpet Hemocyanin (KLH), Tetanus Toxoid (TT), Diptheria Toxoid (DT), Bovine Serum Albumin (BSA), or Human Serum Albumin (HSA) to produce an immunogen.

The immunogenic complexes produced by coupling of the anti-parasitic endocrine product and an immunogenic carrier according to the methods of this invention are useful in a variety of compositions and methods for anti-parasitic vaccination and treatment. More particularly, they can be useful in anti-endoparasitic and anti-ectoparasitic vaccination and methods of treatment.

Administration of such immunogens, or pharmaceutically acceptable derivatives thereof, may be via any of the conventionally accepted modes of administration of agents which exhibit immunogenicity against ectoparasites and endoparasites. These include parenteral administration, such as subcutaneous, intramuscular or intravenous injection, or non-parenteral (oral) administration.

The compositions used in these therapies may also be in a variety of forms. These include, for example, solid, semi-solid and liquid dosage forms, such as powders, liquid solutions or suspensions, suppositories, and injectable or infusable solutions. The preferred form depends on the intended mode of administration and therapeutic application.

The compositions also will preferably include conventional pharmaceutically acceptable carriers and may include other medicinal agents, carriers, adjuvants, excipients, etc., e.g., human or bovine serum albumin or plasma preparations. Preferably, the compositions of the invention are in the form of a unit dose and will usually be administered one or more times a day. The amount of active compound administered as a vaccination or as a medicament at one time, or over a period of time, will depend on the subject being treated, the manner and form of administration, and the judgment of the treating physician or veterinarian. However, an effective dose may be in the range of from about 1 ng to about 1 mg of hormone-protein carrier conjugate, preferably about 100 $\mu$g to about 500 $\mu$g; it being recognized that lower and higher doses may also be useful.

Accordingly, this invention provides a method of vaccination and a method of treatment against parasitic infection in vertebrates including humans, comprising the administration of an immunologically effective amount of a compound of the invention or its immunologically acceptable derivatives. The hormone-carrier conjugates of the present invention, prepared as described above, may be used to immunize humans, dogs, cats, cows, sheep, swine, horses, or other vertebrates by injecting a dosage form of the conjugate, preferably along with a suitable adjuvant such as alum or an acceptable oily adjuvant containing a bio-degradable oil.

Antibodies induced by the hormone-protein conjugate of this invention may be quantitated by suitable serologic assay such as enzyme linked immunosorbent assay (ELISA) that is capable of specific detection of anti-hormone antibody. Such an assay may detect polyclonal antibodies or monoclonal antibodies (produced by standard hybridoma methods) directed against the hormone. The quantitation of said antibodies provides a measure of the immune status of the vaccinated animal(s). An antibody titer obtained by end point dilution of $\geq 1:1000$ dilution on the ELISA assay is indicative of an immune response that will provide protection against challenge with the appropriate parasite.

In order that the invention described herein may be more fully understood, the following examples are set forth. It should be understood that these examples are for illustrative purposes only, and are not to be construed as limiting this invention in any manner.

Example 1

In this example, we illustrate the preparation of one embodiment of an immunogen of this invention according to the method of J. C. Baehr et al. ["A Simple And Sensitive Radioimmunoassay Of Insect Juvenile Hormone Using An Iodinated Tracer", *FEBS Letters*, 69, pp. 123–28 (1976)]. This method may be used for any of the naturally occurring JH. First, we prepared a free acid derivative by subjecting $JH_3$ to alkaline hydrolysis. We dissolved 10 mg of $JH_3$ in 0.25 ml of methanol. We then added 0.4 ml of methanol/2N NaOH (v/v) to the $JH_3$ and allowed the mixture to react overnight.

We titrated the reaction mixture with 1.0M HCl to lower its pH to 7.0 and then we lyophilized it. We then extracted the $JH_3$ acid by adding 1 ml of ethyl acetate to the lyophilate. We removed the ethyl acetate with a pipette and then repeated the ethyl acetate extraction. We pooled the ethyl acetate extracts and then centrifuged the pooled extracts at $10,000 \times g$ to precipitate solids, and then removed the supernatant. We removed the ethyl acetate from the $JH_3$-acid by exposing the solvent to a gentle nitrogen ($N_2$) stream. The solvent evaporated and $JH_3$-acid was deposited as an oily film on the tube wall.

We reacted the $JH_3$ derivative with N-hydroxysuccinimide (NHS) to prepare a NHS-JH ester intermediate. We dissolved 4.5 mg of NHS and 7.9 mg of dicyclohexylcarbodiimide (DCCI) in 1.0 ml of tetrahydrofuran (THF). We then added this mixture to the $JH_3$ and allowed the reaction to proceed overnight (approximate pH=4.5). We added 0.1 ml of 0.2M $Na_2CO_3$ to the mixture to raise its pH from about 4.5 to 9.5. We then centrifuged the reaction mixture at $10,000 \times g$ to pellet precipitates and drew off the supernatant. We evaporated off the THF under nitrogen stream and then added 1.0 ml THF to the extract $JH_3$-NHS ester from the resulting solid material. We repeated the evaporation, extraction and evaporation steps.

In order to prepare the coupled $JH_3$-KLH, we dissolved the $JH_3$-NHS ester in 1.0 ml THF and prepared five (5) 0.2 ml aliquots equivalent to 2.0 mg $JH_3$. We added 0.8 ml THF to increase each 0.2 ml aliquot to 1.0 ml. We dissolved 10 mg of KLH or 10 mg of Bovine Serum Albumin (BSA) in THF/0.01M $Na_2CO_3$ (v/v), to a total volume of 2 ml of solvent. This mixture was added to each aliquot of $JH_3$ and incubated overnight (approximate pH=9.5). We then evaporated off the THF under a gentle air stream and removed the remaining solvent by lyophilization. By comparing molar extinction characteristics of the conjugate at ultraviolet wavelengths of 280 $\mu$m and 260 $\mu$m, we obtained an estimated coupling of 17 molecules of $JH_3$ to each molecule of KLH or BSA.

Example 1A

A more preferred procedure for preparing JH/protein carrier conjugate is described below. We initially prepared the JH for activation using N-hydroxysulfosuccinimide (NHSS) according to the procedure of W. G. Goodman and B. Adams ["Semipreparative Synthesis And Purification Of Juvenile Hormone Acids By High-Performance Liquid Chromatography", *J. Chromatography*, 294, p. 447 (1984)]. We dissolved 10 mg of JH in 6 mls of methanol/1M NaOH (1:1 v/v) and incubated the mixture at 40° C. for 4 hours. We titrated the reaction mixture with 2M HCl to a pH of 5.0. We then extracted the JH acid by adding 6 mls of chloroform/toluene (9:1 v/v). We repeated the extraction of JH acid into the organic solvent mixture four times.

We then activated the JH acid. We dried the pooled chloroform/toluene extracts under $N_2$ gas and resolubilized the JH acid in THF or other suitable organic solvent. We added a four-fold molar excess of NHSS and DCCI to the JH acid and stirred the mixture overnight. The excess NHSS-DCCI reagent was inactivated by adding 20 $\mu$l of 0.2M $Na_2CO_3$ to the reaction mixture and stirring for 4 hours. We removed the excess $CO_3$ and the precipitated cyclourea which was produced by reaction of DCCI with NHSS and JH acid, by drying the reactants under $N_2$ and redissolving the JH-NHSS in THF or other suitable organic solvent. In the preferred embodiment, the amount of THF added is 0.5 ml to the equivalent of 2.5 mg of JH starting material. We then transferred the dissolved JH-NHSS to a glass container which had been previously coated on the inside with the surface active polyethylene glycol (MW=20,000) to ensure that the JH did not stick to the surface. At this stage, we slowly added an additional 1.5 ml of water to each 0.5 ml aliquot of THF-JH-NHSS and stirred the mixture for one hour. Although the preferred solvent ratio is 1 part THF to 3 parts water, other ratios containing at least 25% THF are also suitable.

In this preferred configuration, 5 to 10 mg of KLH, BSA or DT was dissolved in 2 ml of 0.15M NaCl containing 0.001M $Na_2CO_3$ and added to the JH-NHSS dissolved in THF/$H_2O$ (1:3 v/v). We stirred the reactants overnight and then dialyzed the conjugate against 0.15M NaCl, lyophilized it and stored it at $-20°$ C. until using it as vaccine.

Example 2

Example 2 illustrates one embodiment of our method of preparing peptide hormone-protein conjugates.

Peptide hormones may be conjugated to protein carrier by various methods known to the art including carbodiimide, glutaraldehyde, or diazotization methods [see e.g., B. F. Erlanger, "The Preparation Of Antigenic Hapten-Carrier Conjugates: A Survey," *Methods In Enzymology*, vol. 70, pp. 85–104 (1980)].

We conjugated proctolin and adipokinetic hormones through the carboxy-terminus of the peptide hormone to the carrier protein. We dissolved the peptide hormone in 0.15M NaCl containing water soluble NHSS and 1-ethyl-3-3-(3-dimethylaminopropyl carbodiimide (EDCI). After overnight incubation and stirring, we inactivated the NHSS and EDCI with 0.1M $Na_2CO_3$ and dissolved the carrier protein in 0.1M $Na_2CO_3$. We then added buffer (10 mg protein to 1 mg of peptide) and incubated the mixture overnight. We finally separated the conjugate from the other reactants by dialysis against PBS and lyophilized it for storage.

Example 3

In this example, we illustrate the conjugation of beta-ecdysone or ecdysterone to a protein carrier. Our method involves activation of the hormone by formation of an oxime through the double bonded oxygen at carbon 6 [see e.g., Porcheron et al. "Radioimmunoassay Of Arthropod Moulting Hormone: $\beta$-ecdysone Antibody Production And $125_I$-iodinated Tracer Preparation", 1976 FEBS Letters 61: 159–162 which utilizes the oxime intermediate]. This method may also be used for $\alpha$-ecdysone.

We dissolved 5 mg of ecdysterone in 600 $\mu$l of pyridine containing 2% w/v carboxymethoxylamine. After overnight incubation at an elevated temperature, preferably 50° C., we added benzene to the sample to dilute the pyridine. We then removed the pyridine by drying under a nitrogen ($N_2$) stream. The benzene wash is repeated until the pyridine has been removed.

We added ethyl acetate/30% methanol (10v:1v) to the residue. We removed the organic phase containing the ecdysterone, and measured the Optical Density (O.D. 255 $\mu$m) to ascertain the presence of the ecdysterone (O.D. $\geq$ 1.80). The ethyl acetate was removed by $N_2$ stream and the residue was reconstituted in tetrahydrofuran (THF) containing N-hydroxysuccinimide (NHS) and dicyclohexylcarbodiimide (DCI). The latter two reagents may also include their more water soluble forms, N-hydroxysulfosuccinimide (NHSS) and 1-ethyl-3-(3-dimethylaminopropyl carbodiimide) (EDCI).

We then incubated the above reactants for 24–48 hours at room temperature and then added 20 $\mu$l of 0.1M $NaPO_4$ buffer, pH 7.5, to inactivate any free NHS (NHSS) or DCI (EDCI). After adding 10–20 mg of carrier protein (e.g., KLH, BSA) dissolved in 0.1M $NaPO_4$ buffer, pH 7.5 to the ecdysterone-NHS, we stirred overnight. We dialyzed the conjugate against phosphate buffered saline (pH 7.2) and lyophilized it for storage.

Example 4

Example 4 illustrates our in vivo results using the JH immunogen prepared in Examples 1 and 1a, above.

We vaccinated fifty mice, four times at approximately one month intervals with 500 $\mu$g of Juvenile Hormone Immunogen ($JH_3$-KLH) per injection. The initial injection was given intraperitoneally in Freunds Complete Adjuvant. The three remaining injections were given in physiologic saline alternating between subcutaneous and intraperitoneal sites. Two weeks after the second, third and fourth injections, blood was drawn from each mouse and the serum collected. Each serum was assayed for anti-JH antibodies utilizing an ELISA technique and $JH_3$-BSA (Bovine Serum Albumin) as antigen. The spleen from one immunized mouse, which was selected by antibody titer, was removed and its cells were fused to a mouse plasmacytoma line according to published hybridoma methods [B. B. Mishell and S. M. Shiigi, Selected Methods in Cellular Immunology, San Francisco (1980)]. Hybrids producing monoclonal antibodies with specificity for $JH_3$ were cloned and grown according to published procedures. Monoclonal antibodies were collected in quantity from expanded cell cultures.

For testing against C. elegans, we pooled together the sera collected from the mice and used it at 1:200, 1:2,000 or 1:20,000 dilution. For testing monoclonal antibodies, we used 3 $\mu$g of anti-$JH_3$ monoclonal antibody (MCA) from a single culture. We tested the antibodies by incubating eggs of C. elegans (10 eggs $\times$ 5 replicates) in 96 well culture plates containing either 50 $\mu$l of diluted serum or 3 $\mu$g of MCA. The percent mortality of larvae hatching from the eggs, the percentage of the surviving larvae developing to adults, and the egg production of these adults in the presence of the $JH_3$ specific antisera or MCA were compared to the same percentages obtained for worms exposed to sera or a MCA not specific for $JH_3$.

Table 1 demonstrates the larvacidal activity of the anti-$JH_3$ pooled sera and MCA on the C. elegans larvae hatching from eggs. It depicts the percentage of larvae of C. elegans surviving exposure to $JH_3$ specific antibodies. In both instances, less than 50% of the larvae survive exposure to antibody (only at 1:200 dilution of pooled sera).

TABLE 1

| Antibody source | % Larvae surviving for +2 days exposure to Antibody |
|---|---|
| 1:200 pooled serum no anti-$JH_3$ activity | 100% |
| 1:20,000 pooled serum anti-$JH_3$ activity | 100% |
| 1:200 pooled serum, anti-$JH_3$ | 47% |
| 3 $\mu$g MCA, no anti-$JH_3$ activity | 100% |
| 3 $\mu$g MCA, anti-$JH_3$ activity | 42% |

Table 2 describes the effect of anti-$JH_3$ pooled sera and MCA on the further development of larvae not killed by antibody (see Table 1). It depicts the percentage of larvae C. elegans developing to adult stage after $JH_3$ specific antibody treatment for two days. Antibody treatment inhibited and/or delayed development of larvae to adults.

TABLE 2

| Treatment | % Developing to adult (Days required) |
|---|---|
| 1:200 pooled serum, no anti-$JH_3$ activity | 98% (1) |
| 1:20,000 pooled serum, anti-$JH_3$ activity | 99% (2) |
| 1:2,000 pooled serum, anti-$JH_3$ activity | 83% (5) |
| 1:200 pooled serum, anti-$JH_3$ activity | 30% (2) |
| 3 $\mu$g MCA, no anti-$JH_3$ activity | 100% (1) |
| 3 $\mu$g MCA, anti-$JH_3$ activity | 100% (2) |

Table 3 shows the effect of anti-$JH_3$ antibody treatment on egg production by adult worms. It depicts the egg production by surveying adult C. elegans 1–3 days after reaching the adult stage. Pooled antibody and MCA reduced egg production at all concentrations tested.

TABLE 3

| | Egg Production as % Control Day | | |
|---|---|---|---|
| | 1 | 2 | 3 |
| 1:200 pooled serum, no anti-JH$_3$ activity | 100% | 100% | 100% |
| 1:20,000 pooled serum, anti-JH$_3$ activity | 23% | 55% | 60% |
| 1:2,000 pooled serum, anti-JH$_3$ activity | 0% | 15% | 17% |
| 1:200 pooled serum, anti-JH$_3$ activity | 0% | 0% | 10% |
| 3 μg MCA, no anti-JH$_3$ activity | 100% | 100% | 100% |
| 3 μg MCA, anti-JH$_3$ activity | 0% | 17% | 60% |

Example 5

For testing against *Nematospiroides dubius* or *Nippostrongylus brasiliensis*, we infected immunized mice with 200–250 infectious stage larvae (L$_3$). At 10 days (*N. dubius*) or 7 days (*N. brasiliensis*) post infection, we euthanized the mice and excised the small intestines. We then compared the worm burdens between JH-immunized and control (KLH only) immunized mice.

Table 4 shows the effect of prior immunization with JH$_1$, JH$_2$ or JH$_3$ on the reduction in worm burdens of mice challenged with 250 larvae of *N. dubius*. The JH immunized mice experienced a statistically significant decrease in the number of worms recovered at +10 days of infection (p= <0.01). The small intestines likewise demonstrated reduced inflammation and other damage due to the presence of the worms.

TABLE 4

| Immunization | Mean Worm Burden ± SE | % Reduction Versus Control | Pathology in Small Intestine |
|---|---|---|---|
| Control (N = 12) | 244 ± 20 | — | +++ |
| JH$_1$ (N = 12) | 144 ± 16 | 14% | + |
| JH$_2$ (N = 12) | 159 ± 12 | 35% | + |
| Control (N = 9) | 208 ± 12 | — | +++ |
| JH$_3$ (N = 9) | 139 ± 11 | 33% | + |

Table 5 demonstrates the effect of prior immunization with JH$_3$ on the reduction in worm burdens of mice challenged with 200 larvae of *N. brasiliensis*. At 7 days post infection, immunized mice experienced a statistically significant (p= <0.002) reduction in intestinal worm burden. More larvae were recovered from the lungs of immunized mice, indicating their entrapment there.

TABLE 5

| Immunization | Mean Worm Burden ± SE | % Reduction Versus Control | Mean No. of Larvae in Lungs |
|---|---|---|---|
| Control (N = 5) | 59 ± 8 | — | 2 |
| JH$_3$ (N = 5) | 20 ± 3 | 66 | 15 |

Example 6

We fed nymphs and adults of the blood sucking Argasid tick, *Ornithodoros moubata*, on 50 mice immunized with JH$_3$-KLH, with Ecdysterone-KLH, or with KLH only as control. The mice were bled at the time intervals described above.

Table 6 describes the effect on immunized and control mice, of feeding nymphs of *O. moubata* to the mice. We observed a statistically significant reduction in the moulting of first stage nymphs fed blood containing anti-JH$_3$ or ecdysterone antibodies (p<0.01).

TABLE 6

| Immunization | No. of First Stage Nymphs (N1) | Mean % Moulting N1 → N2 |
|---|---|---|
| Control | N = 80 | 96 ± 3 |
| JH$_3$ | N = 124 | 63 ± 3 |
| Ecdysterone | N = 117 | 78 ± 5 |

Example 7

We fed nymphs and adults of the Ixodid tick, *Riphicephabus sangineus*, on 5 rabbits immunized with JH$_3$-KLH or Ecdysterone-KLH as illustrated for mice, above. The rabbits were bled at the time intervals described above.

Table 7 illustrates the effect of feeding female *R. sangineus* on JH$_3$-KLH or Ecdysterone-KLH immunized rabbits. We observed a significantly reduced hatch of larvae from those eggs.

TABLE 7

| Immunization | Mean No. Eggs Per Female | % Hatch |
|---|---|---|
| Control | 3211 | 98.3% |
| JH$_3$ | 2925 | 79.9% |
| Ecdysterone | 3939 | 14.2% |

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

I claim:

1. A method for immunizing against or treating a vertebrate for infection by a nematode parasite which comprises administering to the vertebrate an effective amount of a composition comprising juvenile hormone coupled to an immunogenic protein carrier.

* * * * *